(12) United States Patent
Dao et al.

(10) Patent No.: US 12,171,902 B1
(45) Date of Patent: Dec. 24, 2024

(54) PREPARATION OF A PHOSPHOLIPID COMPOSITION/NANO LIQUID PRODUCT USEFUL IN TREATING BURNS AND INCREASING THE EFFECT OF SCAR HEALING

(71) Applicant: Kim Dung Thi Dao, Ho Chi Minh (VN)

(72) Inventors: Kim Dung Thi Dao, Ho Chi Minh (VN); Binh Cong Dao, Tay Ninh (VN); Tam Cong Nguyen, Ho Chi Minh (VN); Van Bich Nguyen, Ho Chi Minh (VN); Bich Lien Thi Nguyen, Phu Yen (VN); Thoa Thi Dao, Ha Noi (VN); Nhat Vy Dao Nguyen, Ho Chi Minh (VN)

(73) Assignee: DKD INTERNATIONAL PRODUCTION JOINT STOCK COMPANY, Ho Chi Minh (VN)

( * ) Notice: Subject to any disclaimer, the term of this patent is extended or adjusted under 35 U.S.C. 154(b) by 0 days.

(21) Appl. No.: 18/757,539

(22) Filed: Jun. 28, 2024

Related U.S. Application Data

(63) Continuation-in-part of application No. 18/450,414, filed on Sep. 6, 2023, now abandoned, and a continuation-in-part of application No. 18/451,071, filed on Aug. 16, 2023, and a continuation-in-part of application No. 18/611,735, filed on Mar. 21, 2024.

(51) Int. Cl.
| | |
|---|---|
| *A61L 26/00* | (2006.01) |
| *C11C 1/00* | (2006.01) |
| *C12N 9/42* | (2006.01) |
| *C12P 9/00* | (2006.01) |

(52) U.S. Cl.
CPC ....... *A61L 26/0052* (2013.01); *A61L 26/0057* (2013.01); *C11C 1/002* (2013.01); *C12N 9/2437* (2013.01); *C12P 9/00* (2013.01); *C12Y 302/01004* (2013.01); *C12Y 302/01015* (2013.01)

(58) Field of Classification Search
CPC .. C11C 1/002; A26L 26/0052; A26L 26/0057; C12N 9/2437; C12Y 302/01004
See application file for complete search history.

(56) References Cited

U.S. PATENT DOCUMENTS

2016/0367676 A1* 12/2016 Burnam ................. A61P 43/00

OTHER PUBLICATIONS

Palacios et al. Egg-Yolk Fractionation and Lecithin Characterization; JAOCS, vol. 82, No. 8, pp. 571-578. (Year: 2005).*
Setiadi et al. The Effect of Papain Enzyme Dosage on the Modification of Egg-Yolk Lecithin Emulsifier Product Through Enzymatic Hydrolysis Reaction; International Journal of Technology, vol. 2, pp. 380-389. (Year: 2018).*
Yazdi et al. Optimization of the Enzyme-Assisted Aqueous Extraction of Phenolic Compounds From Pistachio Green Hull; Food Science Nutrition, vol. 7, pp. 356-366. (Year: 2019).*

* cited by examiner

*Primary Examiner* — Jeanette M Lieb
*Assistant Examiner* — Paul C Martin

(57) ABSTRACT

A phospholipid composition obtained from the process of forming a homogeneous mixture by mixing (A) a first lecithin extract ingredient with (B) a second lecithin extract ingredient from plants in a predetermined ratio of (1-3):(1-3); and then adjusting moisture of the homogeneous mixture below 10%. In addition, the invention also discloses the phospholipid composition applied to make the nano liquid product containing curcumin have the ability to treat burns and increase the effect of scar healing; wherein the product is used at a dose of 0.05-0.1 mL/cm² of skin, with a frequency of twice daily to reduce the area of the burns, and increase the concentration of hydroxyproline in the skin.

11 Claims, 3 Drawing Sheets

PREPARATION OF A PHOSPHOLIPID COMPOSITION/NANO LIQUID PRODUCT USEFUL IN TREATING BURNS AND INCREASING THE EFFECT OF SCAR HEALING

CROSS-REFERENCE TO RELATED APPLICATIONS

This application is a continuation application of application Ser. No. 18/450,414 entitled "Nano liquid composition containing curcumin have the ability to treating burns and increasing the effect of scar healing and method of manufacturing the same", filed on Aug. 16, 2023, which abandoned status, which is a continuation application claiming priority under 35 U.S.C. § 120 to U.S. patent application Ser. No. 18/451,071 entitled "A phospholipid composition and its use in the nano liquid product containing curcumin have the ability to treating burns and increasing the effect of scar healing", filed on Aug. 16, 2023, which abandoned status, which is a continuation application claiming priority under 35 U.S.C. § 120 to U.S. patent application Ser. No. 18/611,735 entitled "Nano liquid composition containing curcumin have the ability to treating burns and increasing the effect of scar healing and method of manufacturing the same" filed on Mar. 21, 2024. The patent application identified above is incorporated here by references in its entirety to provide continuity of disclosure.

FIELD OF THE INVENTION

The invention relates to the preparation of lecithin. In particular, the present invention relates to preparation of a phospholipid composition/nano liquid product useful in treating burns and increasing the effect of scar healing.

BACKGROUND ART

NanoLiposome is one of the advanced drug delivery technologies of the nanosystem, which has great significance in the pharmaceutical and cosmetic industries. Now, there have been some drugs prepared from NanoLiposome that have been used in clinical practice with many outstanding advantages compared to conventional drug delivery systems. NanoLiposomes are nano-sized spherical particles consisting of one or more double layers of phospholipid membranes surrounding the core containing the active ingredient. Liposomes are considered an ideal transport system with the ability to store, protect, transport, and release active substances to desired locations in the body. Using NanoLiposome as a drug delivery system in the body is a new direction. NanoLiposome technology is applied to anti-cancer drugs, gene fragments, recombinant proteins, etc., based on the pharmacokinetic characteristics of NanoLiposome active substances will be transported to target cells precisely, helping to improve the effective treatment and reducing toxicity compared to traditional drugs. Liposome technology also helps poorly soluble active ingredients penetrate into the small intestine wall, helping the body absorb quickly and increase the effectiveness of treatment.

Lecithin is a phospholipid involved in the composition of cell membranes produced in the liver. Lecithin increases the absorption of food and is a good soluble medium for vitamins A, D, E, and K. Lecithin is found naturally in the body's tissues. It is made up of fatty acids and has many commercial and medical uses. Lecithin is used as an emulsifier in the food, pharmaceutical and cosmetic industries.

Enzyme lipase, also known as triaciglycerol lipase, is an enzyme capable of catalyzing the hydrolysis of long-chain triacylglycerols to diacylglycerol, monoacylglycerol, glycerol, and free fatty acids at the interface between water and organic solvents. In addition, lipase also participates in catalyzing ester translocation reactions and ester synthesis reactions in a low-water environment. Belongs to the group of hydrolase enzymes, specifically cutting ester bonds. Strongly active in emulsifying systems, especially island emulsion systems. At the interface between the aqueous phase and the insoluble phases containing the substrate.

According to Patent No. RU2058787C1, the invention refers to the lecithin preparation method that includes the following steps: hen egg yolks were homogenized in acetone at a temperature from −20 to −25 C for 3 min. The process is repeated 6 times. Then egg yolk is extracted with ethanol at 24-28 C in an inert gas atmosphere for 1.5 hr. Obtained after filtration, the cleared solution is precipitated with cadmium chloride. Precipitate is reprecipitated 5 times with ethanol containing cadmium chloride, dissolved in chloroform, and treated with 30% ethanol solution.

According to Patent No. U.S. Pat. No. 4,157,404A, the invention refers to a process for obtaining yolk lecithin from a raw egg yolk which comprises subjecting a raw egg yolk to extraction with liquid dimethyl ether to obtain an extract and dehydrating the extract to the extent that the water content is not more than 20% by weight, whereby a lecithin-rich fraction is obtained as a separate phase from a neutral lipids-fraction. The isolated lecithin-rich fraction may further be subjected to second-stage dehydration to give a product in which the lecithin content is as high as 50 to 85% by weight.

Chakraborty, D., et al. (in Evaluation of the parameters affecting the extraction of sesame oil from sesame (*Sesamum indicum* L.) seed using soxhlet apparatus) International Food Research Journal 24 (2): 691-695 (April 2017) describe the solvent extraction method was carried out using soxhlet apparatus to extract sesame oil from the sesame seed. The primary processing of sesame seed before oil extraction includes drying, crushing, and separating.

According to Patent No. U.S. Pat. No. 5,955,327, the invention refers to a process for manufacturing vegetable lysolecithins from hydrated lecithin used as a starting material which comprises allowing a hydrolysis enzyme consisting of phospholipase A1 or A2 to act on hydrated lecithin, then adding to the resultant lysolecithin solution acetone in a proportion on a volume basis of either 1 to 4, or at least 5, compare to the water contained in said resultant lysolecithin solution to thereby either float or precipitate the lysolecithin phase, then separating out said lysolecithin phase, followed by the repetition of the acetone extraction procedure to separate for removal free fatty acids by-produced in the said lysolecithin production reaction as well as oil-soluble impurities originated from the starting material.

According to Patent No. CN114532535, the invention refers to the preparation method of curcumin nano-liposome comprises the following steps: (1) weighing soybean lecithin, cholesterol, and curcumin, dissolving in an organic solvent, performing rotary evaporation, and removing the organic solvent to form a film; (2) hydrating the lipid film with phosphate buffer solution to form coarse liposome, and stirring; and (3) standing after ultrasonic treatment, and filtering to obtain the nano liposome.

The above inventions meet the specific purposes and requirements of a technical solution. However, the disclosure of the invention does not in detail the process of lipase enzyme recovery obtained from germinated dragon fruit seeds to break down large molecule proteins into small molecule peptides, speeding up the separation of lecithin and proteins; undisclosed the cellulose enzyme system and the pectinase enzyme were obtained from any microorganism source, as well as the combined germination stimulation method between the enzyme system and GA3, and the technical parameters were also different; besides, specifications related to concentration, time, temperature and order of use in combination of extraction, separation, and purification methods are also different; Liposome preparations containing lecithin extract as emulsifier also differed from the control in lecithin extract composition.

Therefore, it is necessary to create a process of recalling the lipase enzyme obtained from germinated dragon fruit seeds to break down large molecule proteins into small molecule peptides, speeding up the separation of lecithin and proteins.

It is necessary to create a process of making lecithin extract ingredients from egg yolk raw materials and plant materials.

Finally, It is necessary to provide a preparation containing phospholipid composition have the ability to treat burns and increase the effect of scar healing. The invention provides solutions to achieve the above objectives.

SUMMARY OF THE INVENTION

Accordingly, an objective of the present invention is to provide a process of manufacturing a preparation containing phospholipid composition have the ability to treat burns and increase the effect of scar healing comprising steps performed in the following specific orders:
(i) creating a phospholipid composition comprising performing in a specific order from (A) to (E):
   (A) preparing a lipase enzyme preparation extracted from germinated dragon fruit seeds;
   (B) creating a first lecithin extract ingredients;
   (C) creating a second lecithin extract ingredients;
   (D) mixing the first lecithin extract ingredients with the second lecithin extract ingredients in a predetermined ratio of (1-3):(1-3) with stirring combination to obtain a homogeneous mixture;
   (E) adjusting the moisture of the homogeneous mixture to below 10% to obtain the phospholipid composition;
(ii) creating a curcumin nano ingredient;
(iii) creating a foundation mixture by mixing ingredients including:
   a cholesterol component with a first percentage (%) by weight;
   a folic acid component with a second percentage (%) by weight;
   the curcumin nano ingredient with a third percentage (%) by weight;
   a tocopherol component with a fourth percentage (%) by weight;
   a xanthan gum component with a fifth percentage (%) by weight;
   a *Camellia sinensis* extracts ingredient with a sixth percentage (%) by weight;
   an aloe vera extracts ingredient with a seventh percentage (%) by weight; and
   the remainder is the phospholipid composition;
   wherein the percentage (%) by weight is determined by the sum from the first percentage (%) to the seventh percentage (%), plus the percentage (%) of the phospholipid composition to equal 100% of the foundation mixture; and
(iv) mixing the curcumin nano ingredient with the foundation mixture in a ratio of 1:1 for 2-4 hours at 120° C. by emulsifying equipment to obtain the preparations containing phospholipid composition have the ability to treat burns and increase the effect of scar healing;
in which said preparation is used at a dose of 0.05-0.1 mL/cm$^2$ of skin, with a frequency of twice daily to reduce the area of the burns, and increase the concentration of hydroxyproline in the skin;
(v) applying the preparation containing phospholipid composition to the skin of a subject in need thereof.

Another objective of the present invention is to provide a lipase enzyme preparation obtained from germinated dragon fruit seeds include the following steps:
(a1) preparing the germinated dragon fruit seeds by following these steps in order:
   selecting and preparing dragon fruits by predetermined quality guidelines;
   washing, peeling, cutting/chopping said dragon fruits into pieces and soaking with an enzyme solution according a ratio 1:5 at 30° C.-35° C. for 12 hours;
      wherein the enzyme solution is obtained by homogeneously dissolving 1 part of an enzyme preparation with 1000 parts of water;
      wherein the enzyme preparation including 2 parts of cellulase enzyme and 3 parts of pectinase enzyme;
      wherein said cellulase enzyme is the biomass obtained by the process of increasing the biomass of microbial strains including *Bacillus licheniformis* DA 15, *Bacillus subtilis* DA 33, and *Bacillus megaterium* NT09;
      wherein said pectinase enzyme is the biomass obtained by the process of increasing the biomass of microbial strains including *Aspergillus niger* X5, and *Aspergillus niger* X9;
   treating said enzyme-treated dragon fruits by steam at the temperature of 90° C. for 3 minutes;
   scrubbing said steam-treated dragon fruits by multipurpose scrubber separating a part of pure, and a part of seeds;
   soaking the part of seeds with Gibberellic acid (GA3) solution at a ratio of 1:10 for 6 hours at 30° C.-35° C.; wherein GA3 solution is obtained by homogeneously dissolving 0.5 mg of GA3 with 1 L of water;
   incubating said GA3-treated part of seeds at 30° C.-35° C. for 8-12 hours, and maintaining humidity of 75%-80% to obtain the germinated dragon fruit seeds;
(a2) creating a solution after centrifugation by following these steps in order:
   grinding a mixture consisting of ½ part of water and 1 part of the germinated dragon fruit seeds;
   stirring said ground mixture for 30 minutes;
   centrifuging said ground, stirred mixture at 13000 rpm for 10 minutes at 4° C. to obtain a solution; and
(a3) freeze-drying the solution to obtain the lipase enzyme preparation form powder, having an activity of 12-16 TU/mg powder;

Yet another objective of the present invention is to provide a first lecithin extract ingredients comprising performing in a specific order from (a) to (g):
(a) selecting and preparing egg yolks by predetermined quality guidelines, then treating egg yolks by washed with water, and using the sieve to remove membranes of egg yolks;
(b) hydrolyzing said treated egg yolks with a lipase enzyme preparation at 35° C. for 2 hours to create an enzyme-treated egg yolks; wherein the lipase enzyme preparation is 0.05%-1.5% by weight of said treated egg yolks;
(c) adding and homogeneously dissolving acetone solution to the enzyme-treated egg yolks to 5-10 minutes, then let stand at 3° C.-5° C. for 2-3 hours for precipitate phospholipids and proteins;
(d) creating a first precipitate by performing the steps in the following order:
   (d1) filtering said phospholipid and protein precipitate generated at step (c);
   (d2) washing said precipitate at step (d1) with acetone solution, and then filtering; repeating steps of at step (d2) 4 times;
   (d3) removing acetone from said precipitate at step (d2) to create the first precipitate;
(e) creating a second precipitate by adding and homogeneously dissolving 5 parts of ethanol solution with 1 part of the first precipitate at 2° C.-5° C. for 5-8 minutes, and then filtering;
(f) creating a basic mixture by performing the steps in the following order:
   adding and homogeneously dissolving 5 parts of ethanol 91% with 1 part of the second precipitate, and admixing a powder of activated carbon; then let stand for 15 min;
   performing extraction and removing ethanol by rotary evaporator to obtain the basic mixture;
   wherein the powder of activated carbon has 0.005% by total weight of ethanol 91% and the second precipitate; and
(g) creating the first lecithin extract ingredients by performing the steps in the following order:
   adding and homogeneously dissolving 3 parts of petroleum ether with 1 part of the basic mixture and 1 part of acetone, then let stand at 2° C.-5° C. for 1-3 hours;
   removing the solvent layer on the surface, twice extracting by chloroform, and removing the solvent at low pressure to obtain the first lecithin extract ingredients.

Finally, the purpose of the invention is to provide a second lecithin extract ingredients comprising performing in a specific order from (a') to (g'):
(a') creating a first mixture by performing the steps in the following order:
   chopping/cutting 1 part of an avocado by-product and 3 parts of an eggplant (*Solanum melongena*) to obtain a temporary mixture;
   treating the temporary mixture by steam at 100° C. for 5 minutes to obtain a steam-treated temporary mixture;
   grinding the steam-treated temporary mixture to obtain a temporary powder; and
   drying the temporary powder to a moisture content below 7% to obtain the first mixture;
(b') creating a second mixture by performing the steps in the following order:
   admixing 1 part of tomato seeds (*Solanum lycopersicum*) with 1 part of chili seeds and 2 parts of sesame seeds (*Sesamum indicum*) to obtain a seeds mixture;
   treating the seeds mixture by steam at 100° C. for 5 minutes, then grinding to obtain a seeds powder;
   treating the seeds powder by a cellulose-degrading enzyme ingredient at 28° C.-35° C. for 1 hour to obtain an enzyme-treated seeds powder; wherein the cellulose-degrading enzyme ingredient is 0.05%-0.5% by weight of the seeds powder;
   drying the enzyme-treated seeds powder having moisture content below 7% to obtain the second mixture;
(c') adding into the soxhlet extractor consisting of 1 part of the first mixture with 1 part of the second mixture, 1 part of a rice bran having a moisture content less than 7%, and (10-15) parts of ethyl ether solvent; then extracting for 8 hours to obtain a temporary solution and a residue;
(d') creating a first solution by centrifugation of the temporary solution;
(e') creating a second solution by treated the residue with the lipase enzyme preparation at 35° C. for 2 hours, then centrifuging said enzyme-treated residue and removing solvents by vacuum evaporator at 40° C. to obtain the second solution; wherein the lipase enzyme preparation has 0.05%-1.5% by weight of the residue;
(f') creating a foundation solution by adding and homogeneously dissolving the first solution with the second solution, and the powder of activated carbon, then let stand for 15 minutes, and centrifuging; wherein the powder of activated carbon has 0.005% by total weight of the first solution and the second solution; and
(g') creating the second lecithin extract ingredients by performing the steps in the following order:
   (g1') adding and homogeneously dissolving cold acetone (4° C.) into the foundation solution for 5 minutes, then let stand for 3 hours at 5° C. for precipitate lecithin;
   (g2') washing said lecithin precipitate at step (g1') by acetone at room temperature, and then filtering; repeating steps of step (g2') 5 times;
   (g3') adding and homogeneously dissolving cold ethanol with said precipitate at step (g2') to 8-10 minutes; and
   (g4') filtering and removing solvents with vacuum evaporator at 40° C., then twice extracting by chloroform, and removing the solvent at low pressure to obtain the second lecithin extract ingredients.

These and other advantages of the present invention will no doubt become obvious to those of ordinary skill in the art after having read the following detailed description of the preferred embodiments, which are illustrated in the various drawing Figures.

BRIEF DESCRIPTION OF THE DRAWINGS

The accompanying drawings, which are incorporated in and form a part of this specification, illustrate embodiments of the invention and, together with the description, serve to explain the principles of the invention.

DETAILED DESCRIPTION OF THE INVENTION

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill in the art that the present invention may be practiced without these specific details. In other instances, well-known methods, procedures, components, and circuits have not been described in detail so as not to unnecessarily obscure aspects of the present invention.

In the embodiment of the present invention, percent mass or percentage (%) by weight=(mass of solute/mass of solution)×100%. The unit of mass is usually grams. Mass percent is also known as the correct percentage by weight or w/w %. It should also be noted that the molar mass is also within the meaning of the invention. Molar mass is the total mass of all atoms in a mole of compound. Total all volume percentages add up to 100%.

Figure 1:
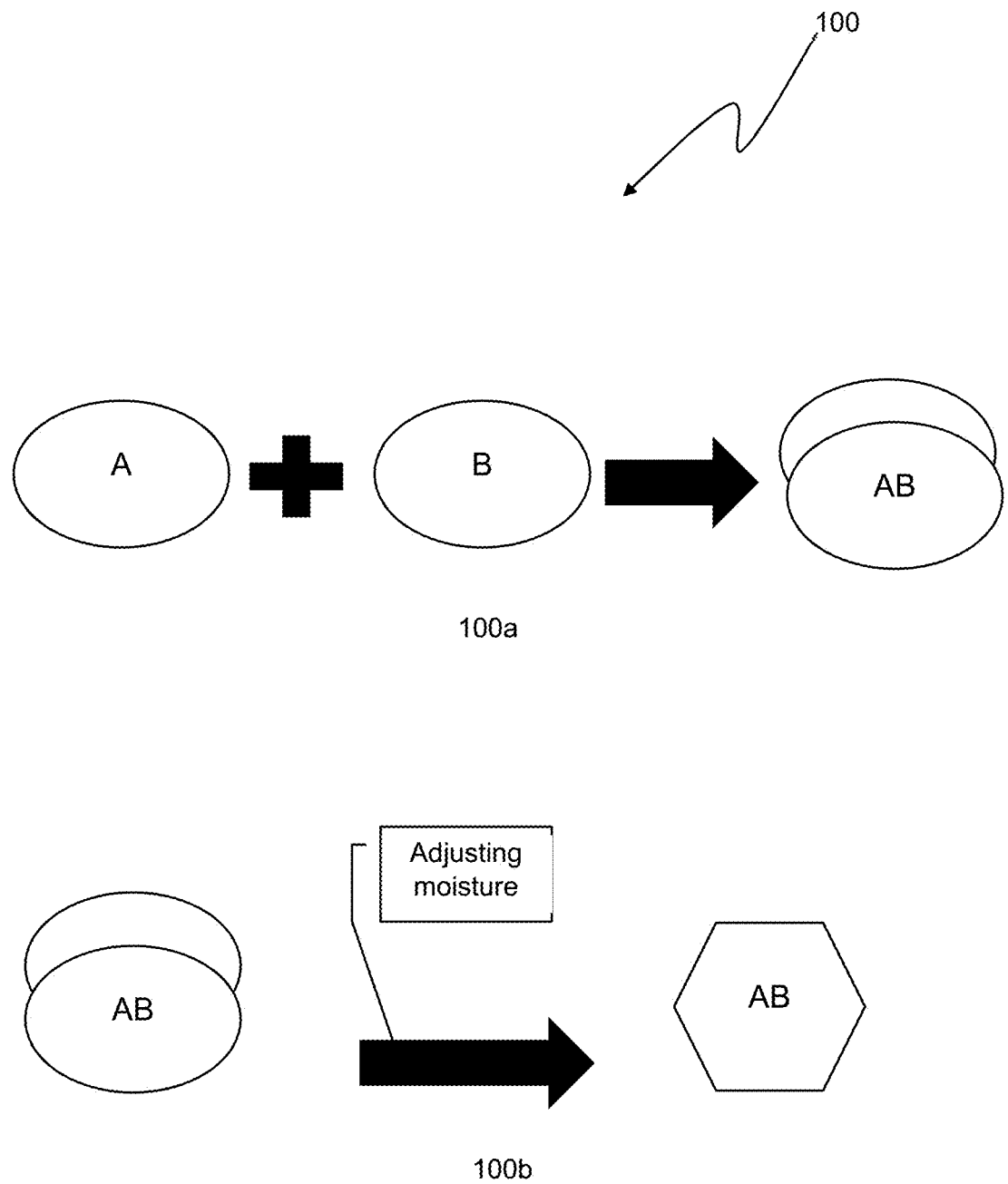
FIG. 1 is a conceptual block diagram illustrating the principle of making the phospholipid composition in accordance with an exemplary embodiment of the present invention.

One embodiment of the invention is now described with reference to FIG. 1. FIG. 1 illustrates a conceptual block diagram of a method 100 including a first stage 100a and a second stage 100b of manufacturing the phospholipid composition in accordance with an exemplary embodiment of the present invention.

In the first stage of 100a, a homogeneous mixture by mixing a first lecithin extract ingredients (A) with a second lecithin extract ingredients (B) in a predetermined ratio of (1-3):(1-3). In many aspects of the present invention, the homogeneous solution is defined as a mixture with the following functions including an emollient (think softening), water-binding agent (to boost hydration), and emulsifying agent (to help water and oil ingredients mesh better in a formula).

In the second stage of 100b, adjusting moisture of the homogeneous mixture below 10% to create a phospholipid composition (AB).

According to the preferred embodiment of the invention, the phospholipid composition (AB) applied to make the nano liquid product containing curcumin have the ability to treat burns and increase the effect of scar healing; wherein the product is used at a dose of 0.05-0.1 mL/cm$^2$ of skin, with a frequency of twice daily to reduce the area of the burns, and increase the concentration of hydroxyproline in the skin.

According to the preferred embodiment of the invention, the first lecithin extract ingredients (A) is obtained by performed in a specific order from (a) to (g) comprising:
(a) selecting and preparing egg yolks by predetermined quality guidelines, then treating egg yolks by washed with water, and using the sieve to remove membranes of egg yolks;
(b) hydrolyzing said treated egg yolks with a lipase enzyme preparation at 35° C. for 2 hours to create an enzyme-treated egg yolks; wherein the lipase enzyme preparation is 0.05%-1.5% by weight of said treated egg yolks;
(c) adding and homogeneously dissolving acetone solution to the enzyme-treated egg yolks to 5-10 minutes, then let stand at 3° C.-5° C. for 2-3 hours for precipitate phospholipids and proteins;
(d) creating a first precipitate by performing the steps in the following order:
  (d1) filtering said phospholipid and protein precipitate generated at step (c);
  (d2) washing said precipitate at step (d1) with acetone solution, and then filtering; repeating steps of at step (d2) 4 times;
  (d3) removing acetone from said precipitate at step (d2) to create the first precipitate;
(e) creating a second precipitate by adding and homogeneously dissolving 5 parts of ethanol solution with 1 part of the first precipitate at 2° C.-5° C. for 5-8 minutes, and then filtering;
(f) creating a basic mixture by performing the steps in the following order:
  adding and homogeneously dissolving 5 parts of ethanol 91% with 1 part of the second precipitate, and admixing a powder of activated carbon; then let stand for 15 min;
  performing extraction and removing ethanol by rotary evaporator to obtain the basic mixture;
  wherein the powder of activated carbon has 0.005% by total weight of ethanol 91% and the second precipitate; and
(g) creating the first lecithin extract ingredients (A) by performing the steps in the following order:
  adding and homogeneously dissolving 3 parts of petroleum ether with 1 part of the basic mixture and 1 part of acetone, then let stand at 2° C.-5° C. for 1-3 hours;
  removing the solvent layer on the surface, twice extracting by chloroform, and removing the solvent at low pressure to obtain the first lecithin extract ingredients (A).

According to the preferred embodiment of the invention, the first lecithin extract ingredients (A) are selected from eggs of various types of poultry including chicken (*Gallus gallus domesticus, Gallus gallus otomesticus*), red-feathered wild chicken (*Gallus gallus spadiceus*), muskuseend (*Cairina moschata forma domestica*), grass goose (*Cynopsis sinensis*), mallard (*Anas platyrhynchos*), and quail (*Coturnix japonica*); all are listed in detail in Table 1 below.

TABLE 1

Scientific name and distribution of types poultry used for egg yolk harvesting as embodiment of the present invention.

| No. | Name | Science name | Distribution |
|---|---|---|---|
| 1 | Chicken | *Gallus gallus domesticus* | Viet Nam |
| 2 | Red-feathered wild chicken | *Gallus gallus spadiceus* | Northwest Viet Nam |

TABLE 1-continued

Scientific name and distribution of types poultry used for egg yolk harvesting as embodiment of the present invention.

| No. | Name | Science name | Distribution |
|---|---|---|---|
| 3 | Chicken | *Gallus gallus tomesticus* | Bac Giang, Hai Phong, Hai Duong . . . |
| 4 | Muskuseend | *Cairina moschata forma domestica* | Red river delta |
| 5 | Grass goose | *Cynopsis sinensis* | Northern Plains and Midlands |
| 6 | Mallard | *Anas platyrhynchos* | Ben Tre, Nghe An |
| 7 | Quail | *Coturnix japonica* | Dong Nai |

According to the preferred embodiment of the invention, the second lecithin extract ingredients (B) comprising an avocado by-product, an eggplant (*Solanum melongena*), tomato seeds (*Solanum lycopersicum*), sesame seeds (*Sesamum indicum*), and a rice bran; all are listed in detail in Table 2 below.

TABLE 2

Scientific names and distribution of plant species used for lecithin extract as embodiment of the present invention.

| No. | Name | Science name | Distribution |
|---|---|---|---|
| 1 | Avocado 034 | *Persea americana* | Bao Loc-Lam Dong |
| 2 | Avocado wax | *Persea americana* 'Maluma' | Dak Lak |
| 3 | Eggplant | *Solanum melongena* | Dak Nong |
| 4 | Sesame seeds | *Sesamum indicum* | Thanh Hoa, Nghe An, Ha Tinh, Quang Binh, Quang Tri |
| 5 | Rice bran | Rice bran | Mekong delta |
| 6 | Celestial chili | Celestial chili | Thanh Binh, Dong Thap |
| 7 | Dangerous chili | *Capsicumn annuum* L | Thanh Binh, Dong Thap |
| 8 | Ba tri chili | Golden Horn Peppers | Ben Tre |
| 9 | Tomato | *Solanum lycopersicum* | Lam Dong |

According to the embodiment of the invention, the second lecithin extract ingredients (B) is obtained by performed in a specific order from (a') to (g') comprising:
- (a') creating a first mixture by performing the steps in the following order:
    - chopping/cutting 1 part of an avocado by-product and 3 parts of an eggplant (*Solanum melongena*) to obtain a temporary mixture;
    - treating the temporary mixture by steam at 100° C. for 5 minutes to obtain a steam-treated temporary mixture;
    - grinding the steam-treated temporary mixture to obtain a temporary powder; and
    - drying the temporary powder to a moisture content below 7% to obtain the first mixture;
- (b') creating a second mixture by performing the steps in the following order:
    - admixing 1 part of tomato seeds (*Solanum lycopersicum*) with 1 part of chili seeds and 2 parts of sesame seeds (*Sesamum indicum*) to obtain a seeds mixture;
    - treating the seeds mixture by steam at 100° C. for 5 minutes, then grinding to obtain a seeds powder;
    - treating the seeds powder by a cellulose-degrading enzyme ingredient at 28° C.-35° C. for 1 hour to obtain an enzyme-treated seeds powder; wherein the cellulose-degrading enzyme ingredient has 0.05%-0.5% by weight of the seeds powder;
    - drying the enzyme-treated seeds powder having moisture content below 7% to obtain the second mixture;
- (c') adding into the soxhlet extractor consisting of 1 part of the first mixture with 1 part of the second mixture, 1 part of a rice bran having a moisture content less than 7%, and (10-15) parts of ethyl ether solvent; then extracting for 8 hours to obtain a temporary solution and a residue;
- (d') creating a first solution by centrifugation of the temporary solution;
- (e') creating a second solution by treated the residue with the lipase enzyme preparation at 35° C. for 2 hours, then centrifuging said enzyme-treated residue and removing solvents by vacuum evaporator at 40° C. to obtain the second solution; wherein the lipase enzyme preparation has 0.05%-1.5% by weight of the residue;
- (f') creating a foundation solution by adding and homogeneously dissolving the first solution with the second solution, and the powder of activated carbon, then let stand for 15 minutes, and centrifuging; wherein the powder of activated carbon has 0.005% by total weight of the first solution and the second solution; and
- (g') creating the second lecithin extract ingredients (B) by performing the steps in the following order:
    - (g1') adding and homogeneously dissolving cold acetone (4° C.) into the foundation solution for 5 minutes, then let stand for 3 hours at 5° C. for precipitate lecithin;
    - (g2') washing said lecithin precipitate at step (g1') by acetone at room temperature, and then filtering; repeating steps of step (g2') 5 times;
    - (g3') adding and homogeneously dissolving cold ethanol with said precipitate at step (g2') to 8-10 minutes; and
    - (g4') filtering and removing solvents with vacuum evaporator at 40° C., then twice extracting by chloroform, and removing the solvent at low pressure to obtain the second lecithin extract ingredients (B).

It should be noted that these apparatus used according to the method 100 in the present invention includes, but is not limited to a centrifuge, a crusher, a filtration equipment, a cutting machines, an emulsifying equipment, a washing machine, a stirring equipment, a multipurpose scrubber, a scrubbers, and others similar devices, that all have been known in previous art so the description of the structure and its operating principle will not be described in detail in the invention.

Figure 2:
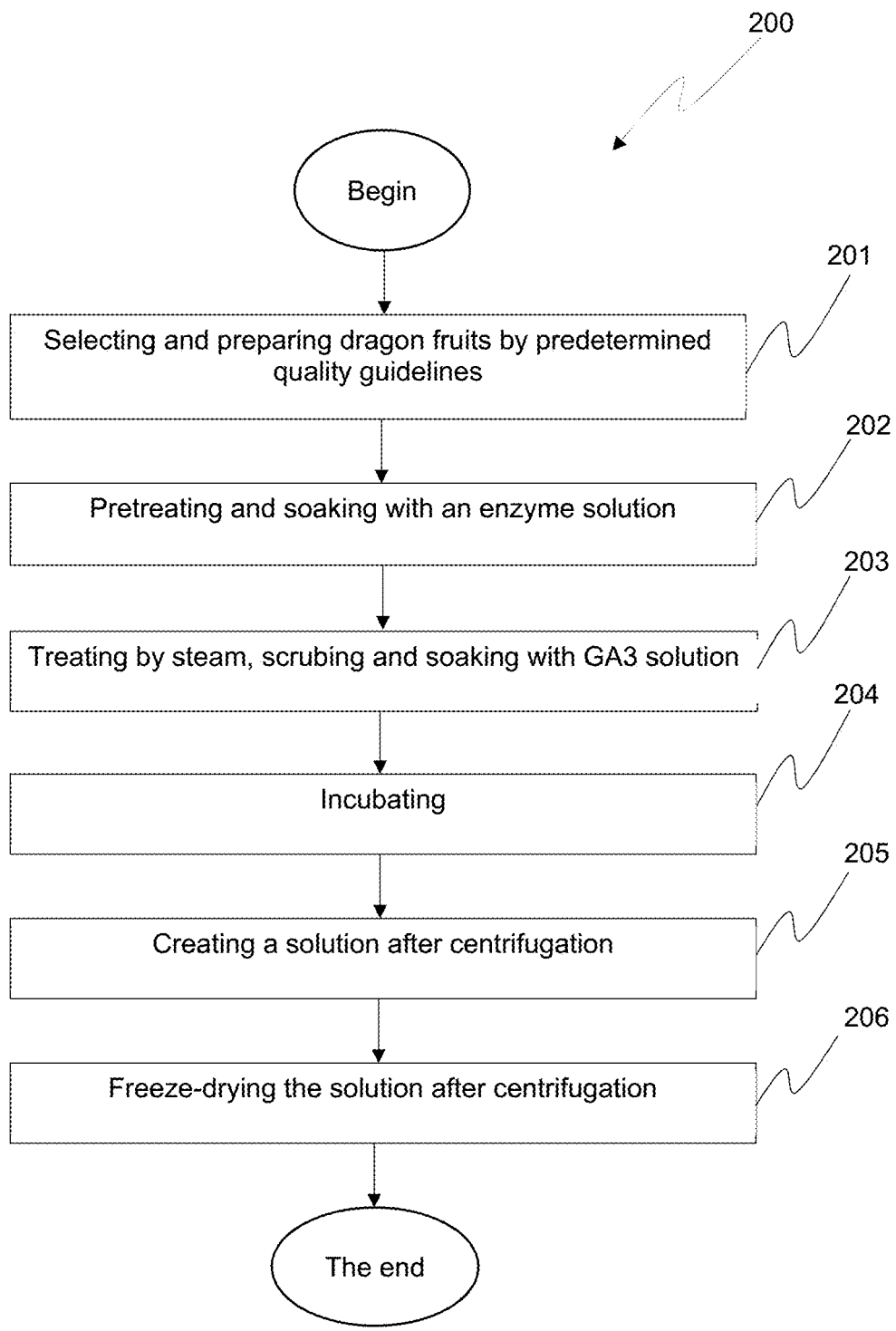
FIG. 2 is a flowchart illustrating a general method of manufacturing the lipase enzyme preparation from germinated dragon fruit seeds in accordance with an exemplary embodiment of the present invention.

Now referring to FIG. 2, the process 200 is the manufacturing the lipase enzyme preparation from germinated dragon fruit seeds in accordance with embodiment of the present invention. Process 200 starts with step 201 which is to select and prepare dragon fruits by predetermined quality guidelines, that include selecting the dragon fruits have a Brix level of at least 10; and performing visual inspection to select said fruits that are ripe, undamaged, heavy, and free of spoilage spots.

According to the preferred embodiment of the invention, the dragon fruits are selected from types of dragon fruits including red flesh dragon fruit (*Hylocereus costaricensis*), white flesh dragon fruit (*Selenicereus undatus*), Gele pitahaya (*Hylocereus megalanthus*), and Purple and pink dragon fruit (*Hylocereus undatus costaricensis*); all listed in detail in Table 3 below.

TABLE 3

Scientific names and distribution of types of dragon fruits used for dragon fruit seeds harvesting as embodiment of the present invention.

| No. | Name | Science name | Distribution |
|---|---|---|---|
| 1 | Red flesh dragon fruit | *Hylocereus costaricensis* | Binh Thuan, Long An, Tien Giang |
| 2 | White flesh dragon fruit | *Selenicereus undatus* | Binh Thuan, Long An, Tien Giang |
| 3 | Gele pitahaya | *Hylocereus megalanthus* | Binh Thuan, Long An, Tien Giang |
| 4 | Purple and pink dragon fruit | *Hylocereus undatus costaricensis* | Binh Thuan, Long An, Tien Giang |

Continuing with FIG. 2, at step 202, pretreating including washing, peeling, cutting/chopping the dragon fruits at step 201 into pieces. Then, soaking said pieces with an enzyme solution according a ratio 1:5 at 30° C.-35° C. for 12 hours. The result in step 202 obtained the enzyme-treated dragon fruits.

According to the embodiment of the invention, the enzyme solution is obtained by homogeneously dissolving 1 part of an enzyme preparation with 1000 parts of water; wherein the enzyme preparation including 2 parts of cellulase enzyme and 3 parts of pectinase enzyme.

According to the preferred embodiment of the invention, cellulase enzyme are obtained from a process proliferation of microbial strains including *Bacillus licheniformis* DA 15, *Bacillus subtilis* DA 33, and *Bacillus megaterium* NT09; all are listed in Table 4 below.

According to the preferred embodiment of the invention, pectinase enzyme are obtained from a process proliferation of microbial strains including *Aspergillus niger* X5, and *Aspergillus niger* X9; all are listed in Table 4 below.

TABLE 4

Microbial strains used for producing cellulase enzyme and pectinase enzyme according to the embodiment of the present invention.

| Features | Name of | References |
|---|---|---|
| Cellulase enzyme | *Bacillus licheniformis* DA 15; *Bacillus subtilis* DA 33; *Bacillus megaterium* NT09. | Trang NT, and Ha NTH, 2015. The grown and synthetic capacity of cellulase by some *Bacillus* strains isolated in VietNam. The 6th national conference one cology and biological resources. |
| Pectinase enzyme | *Aspergillus niger* X5; *Aspergillus niger* X9. | Dung TQ, Cuc NT, Suong NT, and Chung NTT, 2015. Isolation and screening of *Aspergillus niger* strains for biosynthesis of pectianse from peels of some fruits, (banana, apple, mango, dragon and carrot) in Hue city. The 6th national conference on ecology and biological resources. |

At step 203, creating to a GA3-treated part of seeds by treating by steam, scrubbing the enzyme-treated dragon fruits at step 202, then soaking with a Gibberellic acid (GA3) solution. According to the embodiment of the invention, steam-treated dragon fruits obtained by treating the enzyme-treated dragon fruits at step 202 by steam at the temperature of 90° C. for 3 minutes. Then, scrubbing said steam-treated dragon fruits by multipurpose scrubber separating a part of pure, and a part of seeds. The part of seeds is soaked with the GA3 solution at a ratio of 1:10 for 6 hours at 30° C.-35° C. According to the embodiment of the invention, the GA3 solution is obtained by homogeneously dissolving 0.5 mg of GA3 with 1 L of water.

At step 204, incubating the GA3-treated part of seeds at 30° C.-35° C. for 8-12 hours, and maintaining humidity of 75%-80% to obtain the germinated dragon fruit seeds.

At step 205, creating a solution after centrifugation by following these steps in order:
  grinding a mixture consisting of ½ part of water and 1 part of the germinated dragon fruit seeds at step 204;
  stirring said ground mixture for 30 minutes; and
  centrifuging said ground, stirred mixture at 13000 rpm for 10 minutes at 4° C. to obtain the solution.

Finally, at step 206, freeze-drying the solution to obtain the lipase enzyme preparation form powder, having an activity of 12-16 TU/mg powder.

Figure 3:
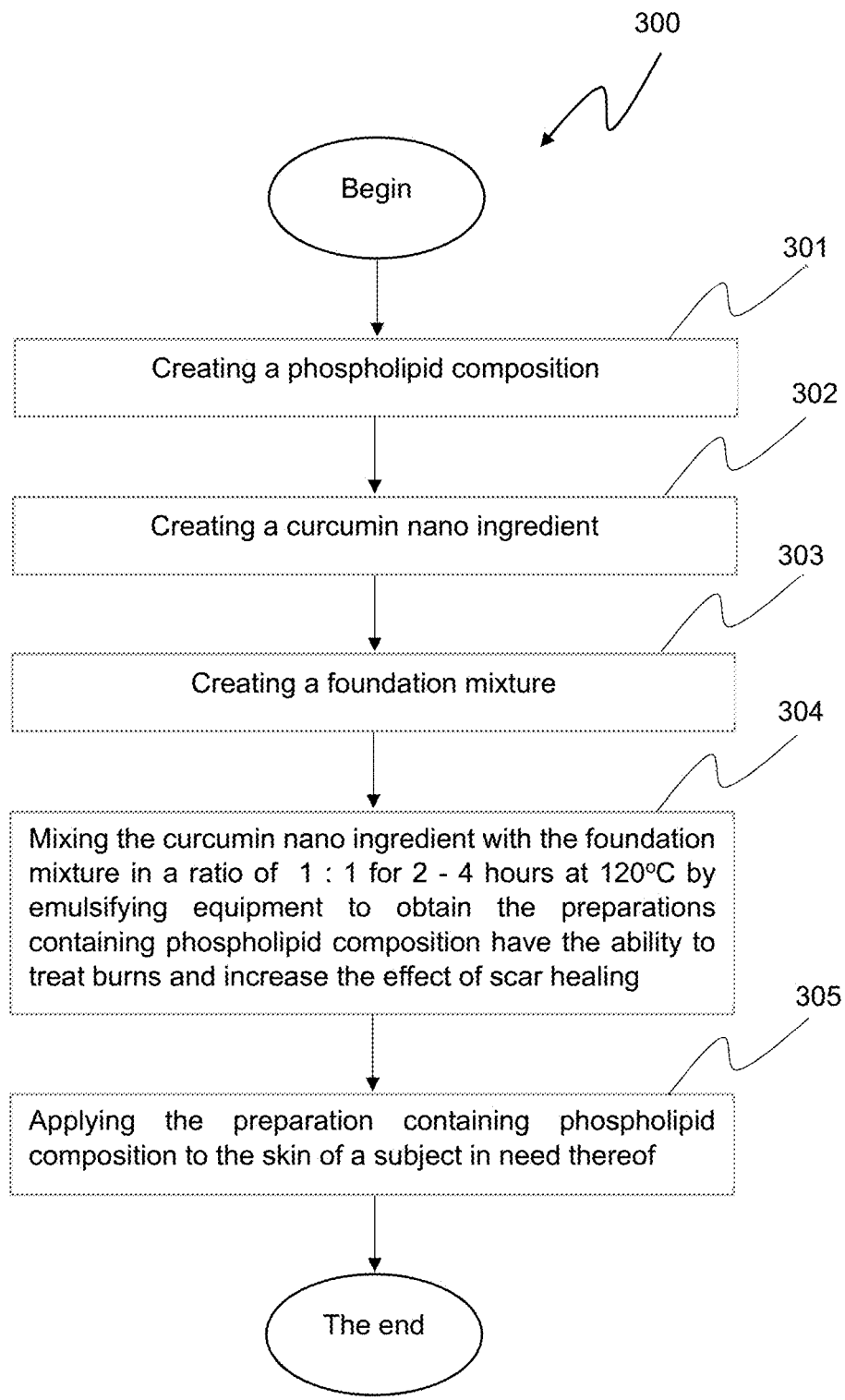
FIG. 3 is a flowchart illustrating the process of manufacturing the preparations containing phospholipid composition have the ability to treat burns and increase the effect of scar healing in accordance with an exemplary embodiment of the present invention.

Refer to FIG. 3, the process of manufacturing the preparation containing phospholipid composition have the ability to treat burns and increase the effect of scar healing 300 ("process 300") in accordance with an exemplary embodiment of the present invention. Process 300 starts with step 301 which is to create a phospholipid composition.

According to the preferred embodiment of the invention, the phospholipid composition is obtained by performed in a specific order from (A) to (E) comprising:
  (A) preparing a lipase enzyme preparation extracted from germinated dragon fruit seeds; wherein the lipase enzyme preparation has been described in detail in process 200 according to an embodiment of the invention;
  (B) creating a first lecithin extract ingredients; wherein the first lecithin extract ingredients is the first lecithin extract ingredients (A) that has been described in detail in method 100 according to an embodiment of the invention;
  (C) creating a second lecithin extract ingredients; wherein the second lecithin extract ingredients is the second lecithin extract ingredients (B) that has been described in detail in method 100 according to an embodiment of the invention;
  (D) mixing the first lecithin extract ingredients with the second lecithin extract ingredients in a predetermined ratio of (1-3):(1-3) with stirring combination to obtain a homogeneous mixture; and
  (E) adjusting the moisture of the homogeneous mixture to below 10% to obtain the phospholipid composition.

At step 302, creating a curcumin nano ingredient by performed in a specific order from (i') to (v') comprising:
  (i') preparing a dispersed phase by dissolving 4 parts of a curcumin with 5 parts of ethanol;
  (ii') creating a carrier mixture by homogeneous dissolving 1.5 parts PEG (polyethylene glycol) with 6 parts EG (ethylene glycol) and 2 parts water, with the combination of ultrasonic vibration for 2 hours at room temperature;
  (iii') creating a homogeneous mixture by homogeneous dissolving 1.6 parts of the dispersed phase at step (i') with 1.5 parts of the carrier mixture at step (ii'), and 2 parts of the phospholipid composition by emulsifying equipment;
  (iv') keeping the homogeneous mixture overnight; and
  (v') centrifuging said homogenized mixture at step (iv') with a speed of 5000 rpm for 10 min, and repeated 6 times of centrifugation to obtain the curcumin nano ingredient form microemulsion.

At step 303, creating a foundation mixture by mixing ingredients including: a cholesterol component with a first percentage (%) by weight;
   a folic acid component with a second percentage (%) by weight;
   the curcumin nano ingredient at step 301 with a third percentage (%) by weight;
   a tocopherol component with a fourth percentage (%) by weight;
   a xanthan gum component with a fifth percentage (%) by weight;
   a *Camellia sinensis* extracts ingredient with a sixth percentage (%) by weight;
   an aloe vera extracts ingredient with a seventh percentage (%) by weight; and
   the remainder is the phospholipid composition at step 302;
wherein the percentage (%) by weight is determined by the sum from the first percentage (%) to the seventh percentage (%), plus the percentage (%) of the phospholipid composition to equal 100% of the foundation mixture.

According to the embodiment of the invention, the foundation mixture comprising:
   the cholesterol component having 18%-25% by weight;
   the folic acid component having 8%-12% by weight;
   the curcumin nano ingredient having 12%-20% by weight;
   the tocopherol component having 2%-5% by weight;
   the xanthan gum component having 2%-5% by weight;
   the *Camellia sinensis* extracts ingredient having 2%-5% by weight;
   the aloe vera extracts ingredient having 0.25%-1% by weight; and
   the remainder is the phospholipid composition.

According to the preferred embodiment of the invention, the foundation mixture comprising:
   the cholesterol component having 21% by weight;
   the folic acid component having 9.5% by weight;
   the curcumin nano ingredient at step 302 having 15% by weight;
   the tocopherol component having 3% by weight;
   the xanthan gum component having 3% by weight;
   the *Camellia sinensis* extracts ingredient having 3% by weight;
   the aloe vera extracts ingredient having 0.5% by weight; and
   the remainder is the phospholipid composition at step 301.

According to the embodiment of the invention, the foundation mixture comprising:
   the cholesterol component having 0.0001% by weight;
   the folic acid component having 0.0001% by weight;
   the curcumin nano ingredient having 50% by weight;
   the tocopherol component having 0.0001% by weight;
   the xanthan gum component having 0.0001% by weight;
   the *Camellia sinensis* extracts ingredient having 0.0001% by weight;
   the aloe vera extracts ingredient having 0.0001% by weight; and
   the remainder is the phospholipid composition.

At step 304, mixing the curcumin nano ingredient at step 302 with the foundation mixture at step 303 in a ratio of 1:1 for 2-4 hours at 120° C. by emulsifying equipment to obtain a preparations containing phospholipid composition have the ability to treat burns and increase the effect of scar healing.

Finally, at step 305, applying the preparation containing phospholipid composition to the skin of a subject in need thereof.

According to the embodiment of the invention, the skin of the subject is animal, or human.

According to the embodiment of the invention, the preparation containing phospholipid composition have the ability to treat burns and increase the effect of scar healing is obtained from process 300 that is used at a dose of 0.05-0.1 mL/cm$^2$ of skin, with a frequency of twice daily to reduce the area of the burns, and increase the concentration of hydroxyproline in the skin.

According to the embodiment of the invention, at step 304 emulsification time is 2 hours.

According to the embodiment of the invention, at step 304 emulsification time is 4 hours.

It should be noted that the term "admixed/mixed/admixing/mixing" as used in the present invention is understood to mean adding, or reacting, or dissolving homogeneously, or evenly, components in the same solution/mixture. The term "homogeneous/homogeneously" is understood to mean the uniform distribution, or complete dissolution of substances present in a solution/mixture/formula.

According to an embodiment taken as an example of the invention, manufacturing 600 Kg of the phospholipid composition by the method 100, including 15 formulas, listed in detail in Table 5 below.

TABLE 5

Mixed ingredients used for manufacturing the phospholipid composition including 15 formulas according to the embodiment of the present invention.

| | Mixed ingredients (Kg) | |
|---|---|---|
| Formula | The first lecithin extract ingredients | The second lecithin extract ingredients |
| 1 | 150 | 450 |
| 2 | 200 | 400 |
| 3 | 225 | 375 |
| 4 | 240 | 360 |
| 5 | 257 | 343 |
| 6 | 267 | 333 |
| 7 | 273 | 327 |
| 8 | 300 | 300 |
| 9 | 327 | 273 |
| 10 | 333 | 267 |
| 11 | 343 | 257 |
| 12 | 360 | 240 |
| 13 | 375 | 225 |
| 14 | 400 | 200 |
| 15 | 450 | 150 |

According to the embodiment of the present invention, investigation of three characteristics of the phospholipid composition including emollient ability, water-binding ability, and emulsifying ability of formulations from 1 to 15. Resulting, formulas 1 to 15 will have said three characteristics ascending in order from 1 to 15. Therefore, the phospholipid composition according to the formula from 1 to 15, applied to make 15 the nano liquid products containing curcumin corresponding; wherein efficiency of treating burns and increasing the effect of scar healing of 15 the nano liquid products will increase gradually in order from 1 to 15.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes" and/or "including," when used in this specification, specify the presence of stated features, integers, steps, operations, elements, and/or components, but do not preclude the presence or addition of one or more other features, integers, steps, operations, element components, and/or groups thereof.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

The description of the present invention has been presented for purposes of illustration and description but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application and to enable others of ordinary skill in the art to understand the invention for various embodiments with various modifications as are suited to the particular use contemplated.

The flow diagrams depicted herein are just one example. There may be many variations to this diagram or the steps (or operations) described therein without departing from the spirit of the invention. For instance, the steps may be performed in a differing order, or steps may be added, deleted, or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

The foregoing description details certain embodiments of the invention. It will be appreciated, however, that no matter how detailed the foregoing appears in text, the invention can be practiced in many ways. As is also stated above, it should be noted that the use of particular terminology when describing certain features or including aspects of the invention should not be taken to imply that the terminology is being re-defined herein to be restricted to any specific characteristics of the features or aspects of the invention with which that terminology is associated. The scope of the invention should therefore be construed in accordance with the appended claims and any equivalents thereof.

What is claimed is:

1. A process of manufacturing a preparation containing phospholipid composition, wherein the composition has the ability to treat burns and increase the effect of scar healing, wherein the method comprises steps performed in the following specific orders:
   (i) creating a phospholipid composition comprising performing in a specific order from (A) to (E):
   (A) preparing a lipase enzyme preparation extracted from germinated dragon fruit seeds include the following steps:
   (a1) preparing the germinated dragon fruit seeds by following these steps in order: selecting and preparing dragon fruits;
   washing, peeling, cutting/chopping said dragon fruits into pieces and soaking with an enzyme solution at a ratio of 1:5 at 30° C.-35° C. for 12 hours;
   wherein the enzyme solution is obtained by dissolving 1 part of an enzyme preparation with 1000 parts of water;
   wherein the enzyme preparation includes 2 parts of cellulase enzyme and 3 parts of pectinase enzyme;
   treating said enzyme-treated dragon fruits by steam at the temperature of 90° C. for 3 minutes;
   scrubbing said steam-treated dragon fruits by multipurpose scrubber, and separating the seeds;
   soaking the seeds with Gibberellic acid (GA3) solution at a ratio of 1:10 for 6 hours at 30° C.-35° C.; wherein GA3 solution is obtained by dissolving 0.5 mg of GA3 with 1 L of water;
   incubating said GA3-treated seeds at 30° C.-35° C. for 8-12 hours, and maintaining humidity of 75%-80% to obtain the germinated dragon fruit seeds;
   (a2) creating a solution after centrifugation by following these steps in order:
   grinding a mixture consisting of ½ part of water and 1 part of the germinated dragon fruit seeds;
   stirring said ground mixture for 30 minutes;
   centrifuging said ground, stirred mixture at 13000 rpm for 10 minutes at 4° C. to obtain a solution; and
   (a3) freeze-drying the solution to obtain lipase enzyme powder, having an activity of 12-16 TU/mg powder;
   (B) creating a first lecithin extract ingredients comprising performing in a specific order from (a) to (g):
   (a) selecting and preparing egg yolks, then treating the egg yolks by washing with water, and removing membranes from said egg yolks;
   (b) hydrolyzing said treated egg yolks with a lipase enzyme preparation at 35° C. for 2 hours to create enzyme-treated egg yolks; wherein the lipase enzyme preparation is 0.05%-1.5% by weight of said treated egg yolks;
   (c) adding and dissolving acetone solution into the enzyme-treated egg yolks for 5-10 minutes, then let stand at 3° C.-5° C. for 2-3 hours to precipitate phospholipids and proteins;
   (d) creating a first precipitate by performing the steps in the following order:
   (d1) filtering said phospholipid and protein precipitate generated at step (c);
   (d2) washing said precipitate at step (d1) with acetone solution, and then filtering;
   repeating steps of at step (d2) 4 times;
   (d3) removing acetone from said precipitate at step (d2) to create the first precipitate;
   (e) creating a second precipitate by adding and dissolving 5 parts of ethanol solution with 1 part of the first precipitate at 2° C.-5° C. for 5-8 minutes, and then filtering;
   (f) creating a basic mixture by performing the steps in the following order:
   adding and dissolving 5 parts of 91% ethanol with 1 part of the second precipitate, then let stand for 15 min;
   (g) creating a first lecithin extract by performing the steps in the following order:
   adding and dissolving 3 parts of petroleum ether with 1 part of a basic mixture and 1 part of acetone, then let stand at 2° C.-5° C. for 1-3 hours forming a surface solvent layer;
   removing the solvent layer, twice extracting with chloroform, and removing the solvent at low pressure to obtain the first lecithin extract;

(C) creating a second lecithin extract comprising performing in a specific order from (a') to (g'):

(a') creating a first mixture by performing the steps in the following order:

chopping/cutting 1 part of an avocado by-product and 3 parts of an eggplant (*Solanum melongena*) to obtain a temporary mixture, wherein the avocado by-product include skins and seeds;

treating the temporary mixture by steam at 100° C. for 5 minutes to obtain a steam-treated temporary mixture;

grinding the steam-treated temporary mixture to obtain a temporary powder;

and drying the temporary powder to a moisture content below 7% to obtain the first mixture;

(b') creating a second mixture by performing the steps in the following order:

admixing 1 part of tomato seeds (*Solanum lycopersicum*) with 1 part of chili seeds and 2 parts of sesame seeds (*Sesamum indicum*) to obtain a seeds mixture;

treating the seeds powder with a cellulose-degrading enzyme at 28° C.-35° C. for 1 hour to obtain an enzyme-treated seeds powder, wherein the cellulose-degrading enzyme is 0.05%-0.5% by weight of the seeds powder;

drying the enzyme-treated seeds powder to a moisture content below 7% to obtain the second mixture;

(c') admixing 1 part of the first mixture with 1 part of the second mixture, 1 part of a rice bran having a moisture content less than 7%, and 10-15 parts of ethyl ether solvent, then extracting for 8 hours to obtain a temporary solution and a residue;

(d') creating a first solution by centrifugation of the temporary solution;

(e') creating a second solution by treating the residue with a lipase enzyme preparation at 35° C. for 2 hours, then centrifuging said enzyme-treated residue and removing solvents by vacuum evaporator at 40° C. to obtain the second solution; wherein the lipase enzyme preparation has 0.05%-1.5% by weight of the residue;

(f') creating a foundation solution by adding and homogeneously mixing the first solution with the second solution, then let stand for 15 minutes, and centrifuging; and (g') creating the second lecithin extract ingredients by performing the steps in the following order:

(g1') adding and homogeneously dissolving acetone at 4° C. into the foundation solution for 5 minutes, then let stand for 3 hours at 5° C. for precipitate lecithin;

(g2') washing said lecithin precipitate at step (g1') with acetone at room temperature, and then filtering; repeating steps of step (g2') 5 times;

(g3') adding and homogeneously mixing ethanol with said precipitate at step (g2') for 8-10 minutes; and (g4') filtering and removing solvents with a vacuum evaporator at 40° C., then twice extracting with chloroform, and removing the solvent at low pressure to obtain the second lecithin extract;

(D) mixing the first lecithin extract ingredients with the second lecithin extract ingredients in a predetermined ratio of 1-3:1-3 with stirring to obtain a homogeneous mixture;

(E) adjusting the moisture of the homogeneous mixture to below 10% to obtain a phospholipid composition;

(ii) creating a curcumin nano ingredient comprising performing in a specific order from (i') to (v'):

(i') preparing a dispersed phase by dissolving 4 parts of a curcumin with 5 parts of ethanol;

(ii) creating a carrier mixture by homogeneously dissolving 1.5 parts polyethylene glycol with 6 parts ethylene glycol and 2 parts water, with ultrasonic vibration for 2 hours at room temperature;

(ii) creating a homogeneous mixture by dissolving 1.6 parts of the dispersed phase at step (i') with 1.5 parts of the carrier mixture at step (ii'), and 2 parts of the phospholipid composition, wherein the homogeneous mixture is created with emulsifying equipment;

(iv') keeping the homogeneous mixture overnight; and (v') centrifuging said homogenized mixture at step (iv') at a speed of 5000 rpm for 10 min, wherein centrifugation is repeated 6 times to obtain the curcumin nano ingredient in the form of a microemulsion;

(iii) creating a foundation mixture by mixing ingredients including:

a cholesterol component with a first percentage (%) by weight;

a folic acid component with a second percentage (%) by weight;

the curcumin nano ingredient with a third percentage (%) by weight;

a tocopherol component with a fourth percentage (%) by weight;

a xanthan gum component with a fifth percentage (%) by weight;

a *Camellia sinensis* extracts with a sixth percentage (%) by weight;

an aloe vera extracts with a seventh percentage (%) by weight;

and the remainder is the phospholipid composition;

wherein the percentage (%) by weight is determined by the sum from the first percentage (%) to the seventh percentage (%), plus the percentage (%) of the phospholipid composition to equal 100% of the foundation mixture;

(iv) emulsifying the curcumin nano ingredient with the foundation mixture in a ratio of 1:1 for 2-4 hours at 120° C. to create a preparation containing phospholipid composition, wherein the preparation has the ability to treat burns and increase the effect of scar healing; and (v) applying the preparation containing phospholipid composition to the skin of a subject in need thereof.

2. The process of claim 1, wherein at step (iv) (v) the preparation is applied at a dose of 0.05-0.1 mL/cm² of skin, with a frequency of twice daily to increase the concentration of hydroxyproline in the skin.

3. The process of claim 1, wherein the dragon fruits are selected from the group consisting of red flesh dragon fruit (*Hylocereus costaricensis*), white flesh dragon fruit (*Selenicereus undatus*), Gele pitahaya (*Hylocereus megalanthus*), and Purple and pink dragon fruit (*Hylocereus undatus costaricensis*).

4. The process of claim 1, wherein the egg yolks are selected from eggs of poultry selected from the group consisting of chicken (*Gallus gallus domesticus, Gallus gallus otomesticus*), red-feathered wild chicken (*Gallus gallus spadiceus*), muskuseend (*Cairina moschata forma domestica*), grass goose (*Cynopsis sinensis*), mallard (*Anas platyrhynchos*), and quail (*Coturnix japonica*).

5. The process of claim 1, wherein the avocado by-product include skins and seeds selected from types of avecade the group consisting of including avocado 034 (*Persea americana*), and avocado wax (*Persea americana* 'Maluma').

6. The process of claim 1, wherein the chili seeds are selected from the group consisting of types of chili including celestial chill, Dangerous chili (*Capsicumn annuum* L.), and Ba tri chili (Golden Horn Peppers).

7. The process of claim 1, wherein at step (iv) emulsification time is 2 hours.

8. The process of claim 1, wherein at step (iv) emulsification time is 4 hours.

9. The process of claim 8, wherein at step (iii) the foundation mixture comprising:
  the cholesterol component having 21% by weight;
  the folic acid component having 9.5% by weight;
  the curcumin nano ingredient having 15% by weight;
  the tocopherol component having 3% by weight;
  the xanthan gum component having 3% by weight;
  the *Camellia sinensis* extracts ingredient having 3% by weight;
  the aloe vera extracts ingredient having 0.5% by weight; and
  the remainder is the phospholipid composition.

10. The process of claim 1, wherein at step (iii) the foundation mixture comprising:
  the cholesterol component having 18%-25% by weight;
  the folic acid component having 8%-12% by weight;
  the curcumin nano ingredient having 12%-20% by weight;
  the tocopherol component having 2%-5% by weight;
  the xanthan gum component having 2%-5% by weight;
  the *Camellia sinensis* extracts ingredient having 2%-5% by weight;
  the aloe vera extracts ingredient having 0.25%-1% by weight; and
  the remainder is the phospholipid composition.

11. The process of claim 1, wherein at step (iii) the foundation mixture comprising:
  the cholesterol component having 0.0001% by weight;
  the folic acid component having 0.0001% by weight;
  the curcumin nano ingredient having 50% by weight;
  the tocopherol component having 0.0001% by weight;
  the xanthan gum component having 0.0001% by weight;
  the *Camellia sinensis* extracts ingredient having 0.0001% by weight;
  the aloe vera extracts ingredient having 0.0001% by weight; and
  the remainder is the phospholipid composition.

* * * * *